United States Patent
Frye et al.

(10) Patent No.: US 12,246,155 B2
(45) Date of Patent: Mar. 11, 2025

(54) SILICON CARBIDE NANONEEDLES AND FABRICATION THEREOF

(71) Applicant: Lawrence Livermore National Security, LLC, Livermore, CA (US)

(72) Inventors: Clint D. Frye, Livermore, CA (US); Mihail Bora, Livermore, CA (US); Adam M. Conway, Livermore, CA (US); Devin Joseph Funaro, Livermore, CA (US); Paulius Vytautas Grivickas, Livermore, CA (US); David L. Hall, San Ramon, CA (US); Lars F. Voss, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1233 days.

(21) Appl. No.: 16/987,121

(22) Filed: Aug. 6, 2020

(65) Prior Publication Data

US 2022/0040463 A1 Feb. 10, 2022

(51) Int. Cl.
*A61M 37/00* (2006.01)
*B81B 1/00* (2006.01)
*B81C 1/00* (2006.01)

(52) U.S. Cl.
CPC ......... *A61M 37/0015* (2013.01); *B81B 1/008* (2013.01); *B81C 1/00531* (2013.01); *A61M 2037/0023* (2013.01); *A61M 2037/0053* (2013.01); *B81B 2201/055* (2013.01)

(58) Field of Classification Search
CPC ...... A61M 37/0015; A61M 2037/0023; A61M 2037/0053; B81B 1/008; B81B 2201/005; B81C 1/00531

USPC .......................................................... 428/367
See application file for complete search history.

(56) References Cited

U.S. PATENT DOCUMENTS

2009/0233445 A1\* 9/2009 Lee ................... C30B 29/60
    438/694
2014/0004443 A1\* 1/2014 Hong ................. H01M 8/1004
    216/13

OTHER PUBLICATIONS

Hexagonal faceted SiC nanopillars fabricated by inductively coupled SF6/O2 plasma method, Materials Science Forum, 2012, 717-720, pp. 893-896.\*
Zhao et al., "Fabrication and characterization of single-crystal 4H—SiC microactuators for MHz frequency operation and determination of Young's modulus," Microelectronic Engineering, vol. 129, 2014, pp. 53-57.
Choi et al., "Fabrication of SiC nanopillars by inductively coupled SF6/O2 plasma etching," Journal of Physics D: Applied Physics, vol. 45, 2012, pp. 10 pages.

(Continued)

*Primary Examiner* — Camie S Thompson
(74) *Attorney, Agent, or Firm* — Zilka-Kotab, P.C.

(57) ABSTRACT

A product includes an elongated carbon-containing pillar having a bottom and a tip opposite the bottom. The width of the pillar measured 1 nm below the tip is less than 700 nm. A method includes masking a carbon-containing single crystal for defining masked regions and unmasked regions on the single crystal. The method also includes performing a plasma etch for removing portions of the unmasked regions of the single crystal, thereby defining a pillar in each unmasked region, and performing a chemical etch on the pillars at a temperature between 1200° C. and 1600° C. for selectively reducing a width of each pillar.

19 Claims, 10 Drawing Sheets

(56) References Cited

OTHER PUBLICATIONS

Davis et al., "Hollow Metal Microneedles for Insulin Delivery to Diabetic Rats," IEEE Transactions on Biomedical Engineering, vol. 52, No. 5, May 2005, pp. 909-915.

Zuuk et al., "Fabrication and characterization of silicon carbide field-emitter array," Microelectronic Engineering, vol. 73-74, Mar. 10, 2004, pp. 106-110.

McAllister et al., "Microfabricated needles for transdermal delivery of macromolecules and nanoparticles: Fabrication methods and transport studies," PNAS, Nov. 25, 2003, vol. 100, No. 24, pp. 13755-13760.

Nordquist et al., "Novel Microneedle Patches for Active Insulin Delivery are Efficient in Maintaining Glycaemic Control: An Initial Comparison with Subcutaneous Administration," Pharmaceutical Research, vol. 24, No. 7, Mar. 27, 2007, pp. 1381-1388.

Yum et al., "Nanoneedle: A multifunctional tool for biological studies in living cells," Nanoscale, vol. 2, Dec. 9, 2010, pp. 363-372.

Qian et al., "Anisotropic Thermal Conductivity of 4H and 6H Silicon Carbide Measured Using TimeDomain Thermoreflectance," Materials Today Physics, vol. 3, 2017, pp. 1-15, retrieved from https://arxiv.org/abs/1712.00830.

Hossain et al., "The fabrication of suspended micromechanical structures from bulk 6H—SiC using an ICP-RIE system," Journal of Micromechanics and Microengineering, vol. 16, 2006, pp. 751-756.

Maboudian et al., "Advances in silicon carbide science and technology at the micro- and nanoscales," Journal of Vacuum Science & Technology A, vol. 31, 2013, pp. 050805-1-050805-18.

Jiang et al., "Fabrication of SiC microelectromechanical systems using one-step dry etching," Journal of Vacuum Science & Technology B, vol. 21, No. 6, Nov./Dec. 2003, pp. 2998-3001.

Ramachandran et al., "Preparation of atomically flat surfaces on silicon carbide using hydrogen etching," Journal of Electronic Materials, vol. 27, 1998, 11 pages.

Powell et al., "Step Structures Produced by Hydrogen Etching of Initially Step-Free (0001) 4H—SiC Mesas, " Materials Science Forum, vols. 483-485, 2005, pp. 753-756.

Soubatch et al., "Structure and Morphology of 4H—SiC Wafer Surfaces after H2-Etching," Materials Science Forum, Feb. 2005, 5 pages.

Frewin et al., "A Comprehensive Study of Hydrogen Etching on the Major SiC Polytypes and Crystal Orientations," Materials Science Forum, vols. 615-617, 2009, pp. 589-592.

Dogan et al., "The effect of hydrogen etching on 6H—SiC studied by temperature-dependent current-voltage and atomic force microscopy," Applied Physics Letters, vol. 85, No. 9, Aug. 30, 2004, pp. 1547-1549.

Stohr et al., "Graphene Ribbon Growth on Structured Silicon Carbide," Annalen der Physik, Apr. 4, 2017, pp. 1-6.

Harrison et al., "Ultradeep electron cyclotron resonance plasma etching of GaN," Journal of Vacuum Science & Technology, vol. 35, No. 6, 2017, pp. 061303-1-061303-7.

* cited by examiner

SILICON CARBIDE NANONEEDLES AND FABRICATION THEREOF

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to silicon carbide nanoneedles, and more particularly, this invention relates to silicon carbide nanoneedles and the top-down fabrication of silicon carbide nanoneedles.

BACKGROUND

Silicon carbide (SiC) is increasingly tasked to perform in electronic and microelectromechanical system (MEMS) devices with demanding requirements due to SiC's wide band gap, high thermal conductivity, high critical breakdown field, high Young's modulus, high resistance to chemical attack, biological compatibility, etc. However, many of the processing techniques that exist for silicon do not work on silicon carbide. For example, silicon carbide is relatively inert and cannot be etched using aqueous solutions. While photoelectrochemical etching and defect selective etching using molten salts at 300° C. to 600° C. may be used, dry etching is the predominant method to etch SiC. Anisotropic etching is typically achieved by plasma etching using a fluorine-based plasma; however, a way to isotropically etch SiC is lacking.

The creation of high power, high frequency switches is important to the development of pulsed-power technologies. Photoconductive silicon carbide switches have been developed and manufactured. Hand polishing is currently used to make optically smooth sidewalls. This process is slow, expensive, and limits performance. The plasma etching and chemical etching techniques disclosed herein reduce the cost and time associated with manufacturing silicon carbide components.

SiC is an attractive material for biological applications due to its chemical inertness and biocompatibility. Crystalline SiC is more stable and less likely to corrode in tissue. SiC nanoneedles, including SiC nano-syringes, may be used in biomedical applications such as for transdermal delivery of drugs and/or proteins. For example, SiC nanoneedles may be beneficial to reduce the toxicity and/or damage caused by traditional transdermal delivery of drugs and/or proteins to delicate body tissues (e.g., muscle tissue, nervous tissue, etc.).

SUMMARY

A product, according to one aspect, includes an elongated carbon-containing pillar having a bottom and a tip opposite the bottom. The width of the pillar measured 1 nm below the tip is less than 700 nm.

A method, according to another aspect, includes masking a carbon-containing single crystal for defining masked regions and unmasked regions on the single crystal. The method also includes performing a plasma etch for removing portions of the unmasked regions of the single crystal, thereby defining a pillar in each unmasked region, and performing a chemical etch on the pillars at a temperature between 1200° C. and 1600° C. for selectively reducing a width of each pillar.

Other aspects and advantages of the present invention will become apparent from the following detailed description, which, when taken in conjunction with the drawings, illustrate by way of example the principles of the invention.

BRIEF DESCRIPTION OF THE DRAWINGS

For a fuller understanding of the nature and advantages of the present invention, as well as the preferred mode of use, reference should be made to the following detailed description read in conjunction with the accompanying drawings.

DETAILED DESCRIPTION

Figure 1:
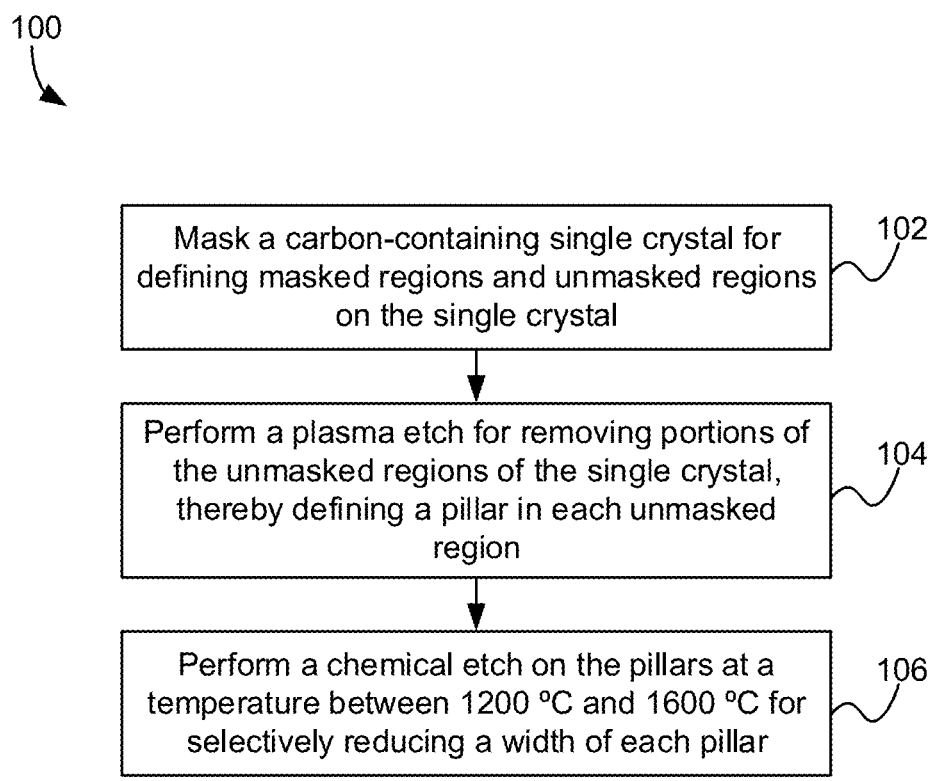
FIG. 1 is a flowchart of a method, according to one aspect of the presently disclosed inventive concepts.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified. The term "about" as used herein indicates the value preceded by the term "about," along with any values reasonably close to the value preceded by the term "about," as would be understood by one of skill in the art. When not indicated otherwise, the term "about" denotes the value preceded by the term "about" ±10% of the value. For example, "about 10" indicates all values from and including 9.0 to 11.0.

The following description discloses several preferred aspects of top-down fabrication of silicon carbide nanoneedles and/or related systems and methods.

In one general aspect, a product includes an elongated carbon-containing pillar having a bottom and a tip opposite the bottom. The width of the pillar measured 1 nm below the tip is less than 700 nm.

In another general aspect, a method includes masking a carbon-containing single crystal for defining masked regions and unmasked regions on the single crystal. The method also includes performing a plasma etch for removing portions of the unmasked regions of the single crystal, thereby defining a pillar in each unmasked region, and performing a chemical etch on the pillars at a temperature between 1200° C. and 1600° C. for selectively reducing a width of each pillar.

Silicon carbide (SiC) is characterized by a uniform lattice structure and strong bonds which make SiC chemically stable. SiC materials are desirable for a number of applications requiring smooth sidewalls. Hand polishing is conventionally used to make optically smooth sidewalls. However, hand polishing generally cannot be performed on nanoscale three dimensional structures, due to the propensity of damage to such structures, the inherent unevenness of such polishing, etc. Hydrogen etching of (0001) surfaces has been well-studied and has become commonplace for surface preparation of SiC substrates prior to homoepitaxy and graphene growth. However, little literature exists on hydrogen etching on non-planar surfaces, such as plasma-etched features. The present disclosure describes an etching process using forming gas or an inert gas with a halogen at high temperatures for producing a smoothing effect on SiC sidewalls (e.g., reducing unwanted sidewall roughness), thereby producing SiC elements in a fraction of the time and with a significant reduction in cost as compared to traditional hand polishing methods, and with minimal damage. The disclosed etching process is useful for such things as removing plasma damage from reactive ion etching, preparing 3D substrates for regrowth, polishing plasma-etched side walls, preparing the surface for homoepitaxy and/or graphene growth e.g., on non-c-face crystal planes, as well as forming sharp needles for field emission, atomic force microscopy cantilevers, electronics, medical devices, etc.

Various approaches described herein include heating SiC to elevated temperatures (e.g., between about 1500° C. and about 1600° C.) where enough energy is supplied such that the SiC will readily react. Forming gas is flowed while at the elevated temperatures, in some approaches. Forming gas, according to various approaches, includes an inert gas and hydrogen as an etchant. In other approaches, an inert gas may be flowed while at elevated temperatures with an etchant such as a diluted halogen gas comprising Cl, Br, I, etc. In yet further approaches, oxygen may be added as an additional etchant to either the forming gas or inert gas/diluted halogen gas mixture. The etchant reacts with silicon and carbide and the products of the reaction are transported away, e.g., according to the exemplary reaction below where hydrogen is in the forming gas.

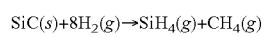

By heating the samples in a high temperature furnace and flowing the inert gas and etchant, the material is removed from the surface of the component in a controlled fashion (e.g., by etching). The procedure disclosed herein may be used, for example, to remove damage caused by a dry etching procedure used to shape the SiC components.

The present disclosure describes a method to fabricate SiC needles with tips as narrow as 15 nm. Various approaches described herein include a method for forming SiC needles by plasma etching micro pillars into single crystal SiC and crystallographically etching the pillars in a high temperature (e.g., greater than about 1300° C.), hydrogen-containing atmosphere.

Now referring to FIG. 1, a flowchart of a method 100 is shown according to one configuration. The method 100 may be performed in accordance with the present invention in any of the environments depicted in FIGS. 2-11B, among others, in various configurations. Of course, more or fewer operations than those specifically described in FIG. 1 may be included in method 100, as would be understood by one of skill in the art upon reading the present descriptions.

As shown in FIG. 1, method 100 includes operation 102. Operation 102 includes masking a carbon-containing single crystal for defining masked regions and unmasked regions on the single crystal. Any conventional etch stop mask which is resistant to plasma etching may be used. Exemplary mask materials include nickel (Ni), aluminum (Al), copper (Cu), chromium (Cr), titanium (Ti), $Al_2O_3$, $Al_2SiO_5$, $SiO_2$, SiN, etc. The carbon-containing single crystal preferably includes a polytype of SiC. In exemplary approaches, the carbon-containing single crystal includes 2H—SiC, 3C—SiC, 4H—SiC, 6H—SiC, etc. Note that operation 102 and other operations of the method 100 may be performed on several single crystals in batch.

Operation 104 includes performing a plasma etch for removing portions of the unmasked regions of the single crystal, thereby defining a pillar in each unmasked region. For example, the single crystal may be etched to form a pillar (or an array of pillars) having cavity regions therebetween, with the array pattern defined by the mask. In various approaches, the etching may be performed all the way through the single crystal. In preferred approaches, the single crystal may be partially etched, such that the resulting etched single crystal includes a planar portion of silicon carbide with pillar(s) extending thereabove. Performing the plasma etch may include techniques such as dry etching by high density plasma (e.g., reactive ion etching) as would be understood by one having ordinary skill in the art.

In various approaches, the pillar includes SiC selected from 2H—SiC, 3C—SiC, 4H—SiC, 6H—SiC, etc. In other approaches, the pillar includes diamond.

In one optional approach of method 100, the mask may be removed using a conventional technique which is compatible with the masking technology used for operation 102. For example, the mask may be removed using solvent dissolution of the mask, deep reactive ion etching, chemical etching (e.g., using an ammonium fluoride-nitric acid solution), via a highly directional plasma etching process, etc.

Operation 106 includes performing a chemical etch on the pillars at a temperature between about 1200° C. and about 1600° C. for selectively reducing a width of each pillar. In preferred aspects, the temperature is between about 1500° C. and about 1600° C. In further preferred aspects, the temperature is between about 1550° C. and about 1600° C. Various attributes of the process may be tuned to affect aspects of the etching, including the content of the flowing gas, the flow rate of the flowing gas, an amount of oxygen introduced into the system, the temperature, etc., or any other tunable characteristic discussed in detail herein.

In various approaches, performing the chemical etch includes contacting the pillars with a gas (e.g., a forming gas, an inert gas and halogen, etc.) having at least one etchant. In preferred approaches, the gas includes an inert gas such as nitrogen ($N_2$), argon (Ar), etc. The gas may include a combination of inert gases. The etchant may include hydrogen (H), chlorine (Cl), bromine (Br), iodine (I), etc.

A preferred range of etchant in the gas is >0 atomic % to about 5 atomic % etchant. In other approaches, the range of etchant in the gas is greater than 5 atomic % etchant. In the case of forming gas comprising hydrogen, higher concentrations may require additional safety measures as would become apparent by one having ordinary skill in the art. In one exemplary approach, the gas having at least one etchant comprises up to 4 atomic % $H_2$ and at least 96 atomic % $N_2$. The etch rate may be strongly influenced by the concentration of etchant in the gas. In various approaches, the ratio between gas and etchant may be adjusted and any equipment modifications may be made, as would become apparent by one having ordinary skill in the art upon reading the present disclosure. For example, the concentration and/or the flow rate of hydrogen changes the etching behavior (e.g., lower hydrogen results in more isotropic etching and higher hydrogen results in crystallographic etching, to be described in further detail below).

In various approaches, the time for performing the plasma etch and/or the chemical etch would be determinable by one having ordinary skill in the art in view of the present disclosure. In preferred approaches, the time for performing the plasma etch and/or the chemical etch may depend on the width of the initial pillars, the depth of the substrate, the flowing gas flow rate, the flowing gas content, the temperature, etc.

In preferred approaches, the plasma etch and the chemical etch (e.g., operations 104 and 106, respectively) are a single-step etch process that removes material as the etching occurs. Note that the single step may include several sub-steps that use the same technique but are performed at different times. This single-step etch process is preferable and more efficient than other potential techniques such as ones that convert an outer surface of the pillar to another material such as an oxide in a first step, and then remove the oxide in a separate, second step. Preferably, the single-step process as described herein is one, single-step etch process without substantial temporal breaks between any sub-steps.

Method 100 optionally includes adding a predefined amount of oxygen to the gas for reducing an extent of crystallographic etching. In various approaches, the oxygen is added to the gas in the form of oxygen gas, water, aluminum oxide, etc. For example, a chemical reduction of aluminum oxide with hydrogen in a furnace may liberate oxygen. Oxygen added to the gas may oxidize the SiC surface in a competing surface reaction with hydrogen etching to form an involatile $SiO_2$ film. The $SiO_2$ film may be used to control the extent of crystallographic etching by mediating the etching via diffusion limited reactions through the film. In general, the higher the amount of oxygen in the gas, or the more resident time the oxygen has to react, the more isotropic (e.g., less crystallographic) the etching. In the case of etching initially round pillars, addition of oxygen tends to shift the peripheral shape from polygonal to round. The change in etching characteristics by inclusion of oxygen was surprising and unexpected. It was surprising that the increase in oxygen (e.g., concentration and/or flow rate) resulted in a less faceted pillar structure. One skilled in the art would expect that the pillar would become more faceted with a substantially flat top with the addition of oxygen. As the sides are etched further to come to a point, one skilled in the art would expect there to be a preference for vertical pillars having substantially flat tips before coming to the point. Again, controlling the amount of oxygen in the etching process as described herein unexpectedly resulted in rounding of the tips of the pillars and/or rounding of the pillars.

In various approaches, the resulting pillar(s) formed by a least some of the operations of method 100 have no oxidation on an outer surface thereof. For example, the oxidation resulting from the addition of oxygen and the surface reaction is completely removed from the outer surface of the pillar as the pillar is etched.

A product formed by at least some of the operations of method 100 includes an elongated carbon-containing pillar having a bottom and a tip opposite the bottom wherein the width of the pillar measured 1 nm below the tip is less than 700 nm. In some aspects, the width of each pillar measured 1 nm below the tip is less than 100 nm. In preferred aspects, the width of each pillar measured 1 nm below the tip is less than 30 nm. In other approaches, the width of the pillar may be measured 5 nm below the tip. In yet other approaches, the width of the pillar may be measured 10 nm below the tip.

Because the pillars are formed from a single crystal of silicon carbide, such crystals have characteristics of formation from a single crystal. For example, the pillar may extend from a single crystal substrate having a bulk composition that is the same as the bulk composition of the pillar (see FIG. 2). Specifically, the pillar extends at its bottom from a single crystal substrate planar portion having a bulk composition that is the same as the bulk composition of the pillar. This approach is contrasted with pillars etched into a silicon substrate and converted to SiC, which have a different structure than pillars formed according to the present methodology, as would be understood by one having ordinary skill in the art in view of the present disclosure. For example, carburizing Si results in only a 3C—SiC polytype. Carburization of silicon also causes stress in the SiC due to the heteroepitaxial nature of the structure, and defects tend to form in the SiC.

Starting with a single crystal provides a number of advantages including the flexibility to start with the SiC polytype that is desired (e.g., 6H—SiC, 4H—SiC, 3C—SiC, etc.) and the tips will be of the same polytype. Another advantage of using a bulk crystal is that the material is easily doped before pillars are fabricated. The pillars, needles, syringes, etc., have the same doping properties of the bulk material. It would be difficult to controllably dope carburized silicon.

A product formed by at least some of the operations of method 100 comprises pillars which have no higher concentration of defects per unit volume than the single crystal substrate. In other words, the single crystal substrate and the pillar have substantially the same concentration of defects per unit volume where the substrate and the pillars are similarly processed.

In contrast, techniques having oxidation of silicon remaining on the outer surface of the pillar post-etching tend to form defects where the coefficient for thermal expansion for $SiO_2$ (e.g., $5.6 \times 10^{-7}$/K) is less than for the coefficient for thermal expansion for SiC (e.g., $4.0 \times 10^{-6}$/K). The difference in thermal expansion between the oxidized outer surface of the pillar and the pillar causes strain within the pillar and a corresponding higher concentration of defects in the pillar compared to a concentration of defects in the substrate.

In some approaches, the pillar has a faceted peripheral outer surface. In some approaches, the pillar has a faceted peripheral outer surface for a majority of the length of the outer surface. For example, the faceted peripheral outer surface may have a hexagonal cross-sectional profile.

In other approaches, the pillar has a rounded peripheral outer surface, e.g., due to the aforementioned inclusion of oxygen in the gas. In preferred approaches, the peripheral outer surface of the pillar is rounded therealong from the bottom to the tip of the pillar. For example, the peripheral outer surface of the pillar is preferably rounded for the entire height, h, of the pillar In preferred approaches, the pillar has a rounded peripheral In outer surface for a majority of the length of the outer surface. For example, the rounded peripheral outer surface may have a circular, oval, oblong, etc., cross sectional profile.

In various other approaches, the pillar may have any other peripheral outer surface shape, including complex shapes. In any of the above approaches, the final shape of the peripheral outer surface of the pillar is defined by the masking of the base crystal from which the pillar is formed. Other exemplary pillars may have an elongated tip extending as a blade in a direction perpendicular to the longitudinal axis of the pillar, a peripheral outer surface in the shape of a rectangle, a peripheral outer surface in the shape of a triangle, etc.

In some approaches, the pillar has an inner channel extending along a longitudinal axis thereof. Such pillar may be generally cylindrical, with any desired cross-sectional shape, such as round, oval, polygonal, faceted, etc. In these approaches, the width of the pillar is considered to be the average width along the rim as measured at one or more points therealong and 1 nm down, as opposed to the diameter of the entire upper end of the "hollow" pillar. The tip width of a pillar having an inner channel extending down from the upper end thereof should not be interpreted to be the diameter of the pillar as a whole unless otherwise specifically disclosed herein.

In some approaches, the pillar with internal channel extends from a single crystal substrate having a bulk composition that is the same as the bulk composition of the pillar, as described above, where the substrate has a channel therethrough in fluid communication with the channel of the pillar. The channel may extend through the pillar and the substrate such that a fluid (e.g., liquid, gas, etc.), may flow through the substrate to the internal channel of the pillar and/or vice versa. Such aspects may be useful for medical applications, such as drug delivery systems, sample collection devices, and others mentioned below.

In preferred approaches, various operations of method 100 may be used to form a product. The product may include an array of pillars, of any type described herein including combinations of differing types, extending from a substrate, where the pillars and the substrate have the same bulk composition. The pillars and the substrate preferably have the same bulk composition throughout the structure. In some approaches, at least some of the pillars in the array of pillars have an inner channel extending a longitudinal axis thereof, as described in detail above. The substrate may have corresponding channels for at least some of the pillars which have channels.

Optional products comprising inner channels through the pillars and/or the substrate which may be further processed for forming nanoneedle and/or microneedle syringes in at least some approaches. For example, a ring-shaped mask (e.g., having an outer diameter and an inner diameter) may be applied for the initial plasma etching, resulting in a cylindrical pillar having an inner channel. The resulting cylindrical pillar may be chemically etched according to the operations above to produce a sharp tip having an opening for the inner channel. The resulting syringe-like tip is preferably tapered from the tip down to at least 1 nm below the tip. In other approaches, the resulting syringe-like tip may be scaled to larger sizes in a continuum of sizes as would become apparent by one having ordinary skill in the art upon reading the present disclosure. The inner diameter of the final cylindrical pillar should be at least large enough to allow travel of the substance of interest therethrough.

The resulting pillars formed by at least some of the approaches of method 100 may be harvested from the substrate in any manner known in the art. In preferred approaches, the pillars are diced out using sawblades according to conventional procedures.

Figure 2:
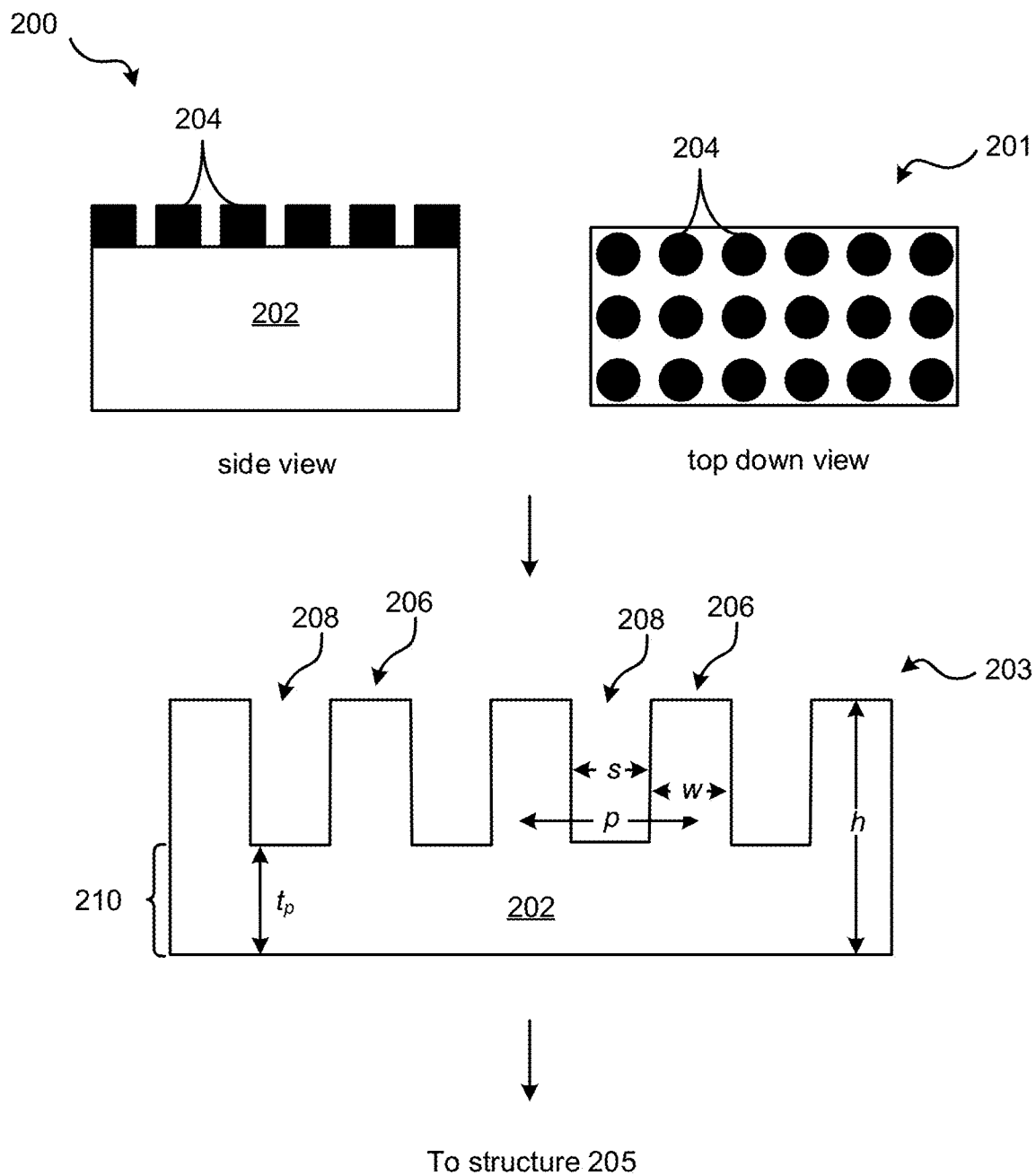
FIG. 2 is a schematic of an exemplary product at various stages of processing, according to one aspect of the presently disclosed inventive concepts.
Figure 2:
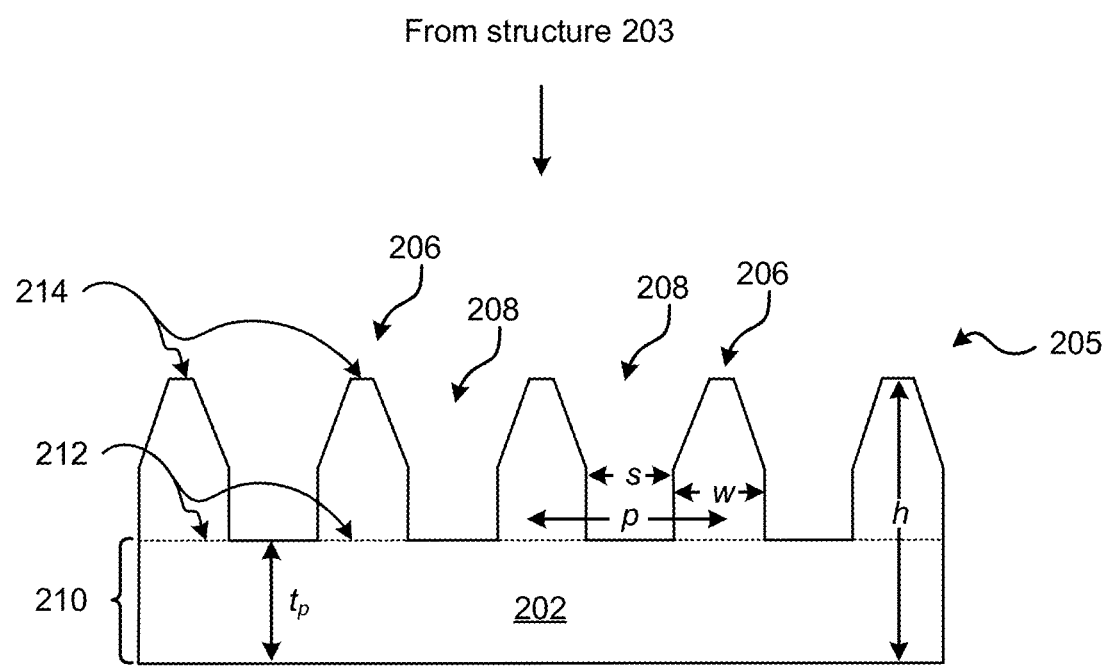

An exemplary product 200 formed by at least some of the operations of method 100 is shown in FIG. 2. As shown in FIG. 2, a carbon-containing single crystal 202 is provided and a mask 204 is applied to an upper surface thereof. See resulting structure 201. In various approaches, the carbon-containing single crystal 202 may include a material including, but not limited to: 2H—SiC, 3C—SiC, 4H—SiC, 6H—SiC, etc.

As also shown in FIG. 2, the carbon-containing single crystal 202 is then etched to form an array of pillars 206 having cavity regions 208 therebetween, with the array pattern defined by the mask 204. The mask 204 may then be removed. See resulting structure 203.

In various approaches, the carbon-containing single crystal 202 may be etched all the way through the carbon-containing single crystal 202, e.g., down to an underlying substrate. In preferred approaches, the carbon-containing single crystal 202 is partially etched such that the single crystal includes a planar portion 210 with the pillar(s) 206 extending thereabove. In approaches where the carbon-containing single crystal 202 is partially etched into the carbon-containing single crystal 202, a thickness, $t_p$, of the planar portion 210 may be in a range from greater than 0 μm to about 500 μm, but $t_p$ could be higher.

It is important to note that the geometry, arrangement, and cross-sectional shape of the pillars 206 are not limited to any particular configuration (e.g., such as the flat top pillars as shown in FIG. 2). For example, in various approaches, the cross-sectional shapes of the pillars may include, but are not limited to: a square, octagon, hexagon, star, triangle, circle, ellipsoid, etc., or other such suitable shapes.

In preferred approaches, the pillars 206 may include a rounded cross-sectional shape, where the cross section is taken perpendicular to longitudinal axes of the pillars 206. In some approaches, a pillar 206 with a rounded cross-sectional shape may be formed using a mask with the rounded feature therein. Alternatively, in other approaches, the mask may contain sharp corners thereby producing pillars 206 with sharp corners that may subsequently be rounded, e.g., by overexposure during the lithographic exposure step, photoresist reflow, wet etching or plasma etching, etc.

The center-to-center pitch, p, between adjacent pillars 206 may be any desirable distance, as set during the masking step. In some approaches, the pitch, p, between at least two adjacent pillars 206 may be in a range from about 0.5 µm to about 10 µm. In other approaches, the pitch, p, between at least two adjacent pillars 206 may be greater than 100 µm, greater than 1000 µm, etc. Further, the edge to edge separation, s, between at least two adjacent pillars 206 may be in a range from about 0.001 µm to about 10 µm. In yet more approaches, the separation between at least some (e.g., less than a majority), a majority, or all of the pillars 206 may be about uniform. For instance, in one approach, the array of pillars 206 may be arranged in a hexagonally close packed (HCP) array. However, in other approaches, the separation between at least some (e.g., less than a majority), a majority, or all of the pillars 206 may not be uniform.

In still more approaches, each of the pillars 206 preferably has a maximum width, w, in a range from about 0.03 µm to about 0.7 µm. The maximum width, w, may vary for different applications as would become apparent by one having ordinary skill in the art upon reading the present disclosure. For example, for electron field emitters the lower bound may be effectively atomically sharp (e.g., about 0.3 nm). In another example, for an array of syringes for drug delivery in the form of a patch with an array of hollow microneedles, the hole in the tip of the syringe may be on the order of about 50 µm to about 80 µm and the outermost diameter (e.g., width, w) may be in the range of about 80 µm to about 300 µm. The pitch in this example is between about 150 µm to 200 µm or greater. The maximum width, w, may be determinable by one having ordinary skill in art in view of the present disclosure and the desired application.

Each of the pillars 206 may also have a height, h, of about 0.1 µm to about 100 µm. In preferred approaches, each pillar has a height, h, of about 50 µm. The height, h, may vary for different applications as would become apparent by one having ordinary skill in the art upon reading the present disclosure. For example, for electron emitters, the lower bound for the height, h, may be about 0.1 µm. In another example, for microsyringes in biological applications, the lower bound for the height, h, may be about 25 µm. The height of the pillars may be as large as the plasma etching allows, in some approaches, as would become understood by one having ordinary skill in the art upon reading the present disclosure. For example, the height, h, may be in the range of about 25 µm to about 400 µm in some approaches. Each of the pillars 206 may additionally have a high aspect ratio of length:average outer diameter in a range from about 2:1 to about 100:1 (e.g., about 10:1, about 25:1, about 50:1, about 100:1, etc.) or higher.

A chemical etch is performed on the structure 203 (see operation 106 of method 100) for forming the exemplary product. See resulting structure 205.

Each pillar 206 includes a bottom 212 and a tip 214 opposite the bottom 212. The width of each pillar 206 measured 1 nm below the tip is less than 700 nm. In some aspects, the width of each pillar 206 measured 1 nm below the tip is less than 100 nm. In preferred aspects, the width of each pillar 206 measured 1 nm below the tip is less than 30 nm.

The tip 214 is generally pointed, where generally pointed refers to a tip which is sharp, a tip which has a flat end, or any sharpness in between but having an outer periphery that tapers together toward the very tip (e.g., based on a measure of the width and radius of the apex of the tip, in some approaches). In some aspects, the sharpness of the point may be determined by measuring the penetration force of a needle into a known medium according to standard procedures known in the art.

In preferred approaches, the tip 214 is rounded. Rounded tips preferably refer to tips which have no facets at all. In some approaches, rounded tips refer to tips which have a perfect circular shape. In other approaches, rounded tips refer to tips which have a perfect ovoidal shape or perfect elliptical shape. "Rounded" as referred to throughout the present disclosure means that no discernable edge is created between the relevant adjacent portion of the outer surface of the pillar. Where the tip is rounded, there is no edge where the top of the pillar meets the peripheral sidewalls of the pillar. For example, see FIG. 11A. The top 1102 of the rounded pillar has no discernable edge which is created between the relevant adjacent portion of the outer surface 1104 of the pillar. There is no intersection of any planes, especially between an m-plane and a c-plane.

Figure 11B:
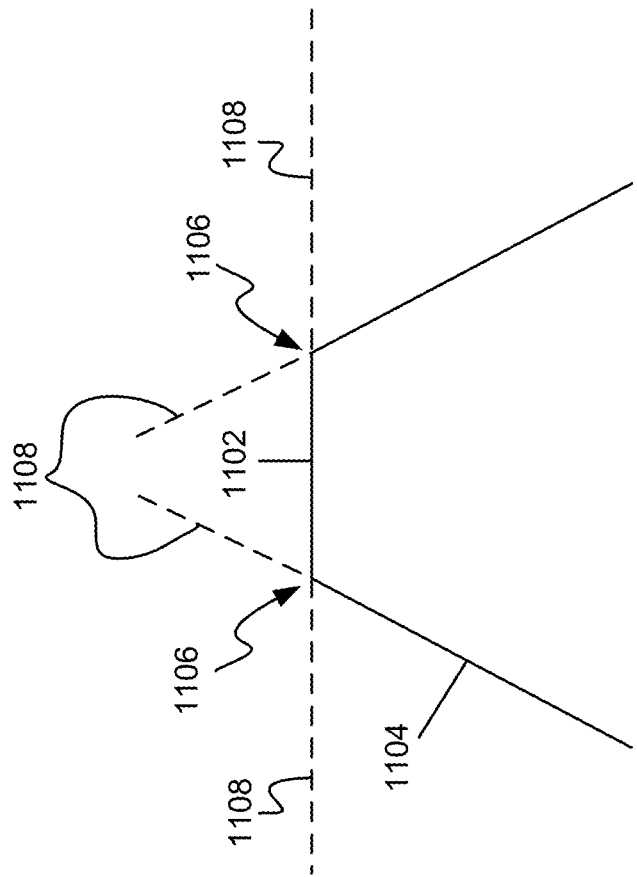
FIG. 11B is a schematic of a faceted tip, according to one aspect of the presently disclosed inventive concepts.
Figure 11A:
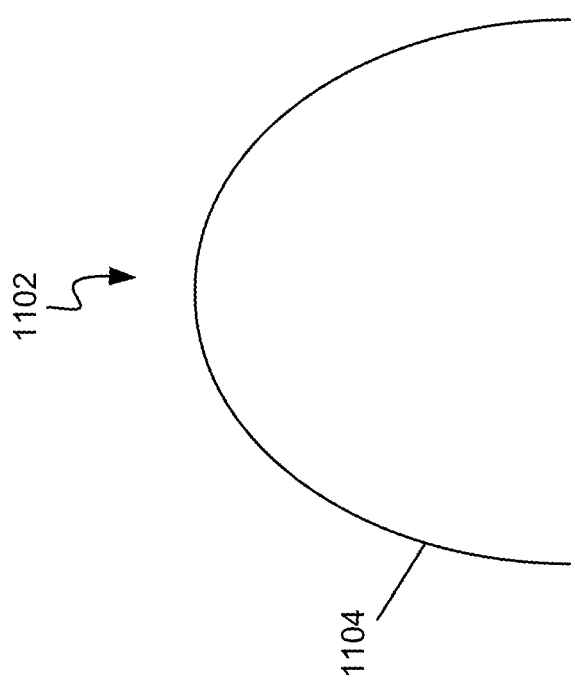
FIG. 11A is a schematic of a rounded tip, according to one aspect of the presently disclosed inventive concepts.

In contrast, FIG. 11B shows a faceted tip where the top 1102 of the pillar has a generally flat tip. The relevant adjacent sidewalls of the pillar which comprise the outer surface 1104 of the pillar form edges 1106 between the planes 1108 generally extending along the substantially flat surfaces of the top 1102 and the outer surface 1104.

In one illustrative aspect, 3D-structures plasma-etched in 4H— and 6H—SiC are etched in forming gas (4% $H_2$, 96% $N_2$) between about 1500° C. and about 1600° C. to produce both faceted surfaces and rounded surfaces. The hydrogen reacts with the SiC to form volatile etch products such as $SiH_4$ and $CH_4$ which are swept away from the substrate by the flowing gas. As the micro pillars etch, the pillars become narrower until the desired width is achieved. This process is controllable to form extremely sharp tips as narrow as 15 nm and, in some approaches, less, by selecting a crystallographically anisotropic etch. The inventors observed that, at higher forming gas flow rates, the etch was anisotropic with the a-planes etching faster than the other planes. The micro pillars become faceted nanoneedles. The etch may be tuned to create a more isotropic etch to produce rounded tips with a tip radius of less than about 700 nm. For example, at lower flow rates, the etch is more isotropic. Sharp 4H—SiC needles with tips as narrow as 15 nm were produced according to at least some of the approaches described herein. The following experimental details are provided by way of example only, and should not be deemed limiting.

Experimental

2 µm wide and 5 µm tall pillars were etched into 4H—SiC chips using an $SF_6$ plasma in a Plasma Quest electron cyclotron plasma etcher (Plasma Quest Limited, Unit 1B Rose Estate, Osborn Way, Hook, Hampshire, RG27 9UT, United Kingdom) (20 standard cubic centimeters per minute (sccm) $SF_6$, 2 mTorr, 850 W ECR power, 130 W RF power for 15 min). Additional 6H—SiC samples were fabricated with various patterns, including rings and ridges rotated every 5 degrees about the c-axis. The 6H—SiC was etched using an $SF_6$—$O_2$ plasma in an ULVAC plasma etcher (401 Griffin Brook Drive, Methuen, MA 01844, USA) to reach a depth of 10 µm (92 sccm $SF_6$, 51 sccm $O_2$, 10 mTorr, 900 W antenna power, 220 W RF power for 17 min). In all cases, the SiC substrates were masked with an electron beam evaporated 200 nm thick nickel hard mask with a 20 nm thick chromium adhesion layer. After plasma etching, the hard mask was stripped using Nickel Enchant Type 1

(Transene Company, Inc., Danvers Industrial Park, 10 Electronics Avenue, Danvers, MA 01923, USA) and CR-7 (Cyantek Corporation, 3055 Osgood Court, Fremont, California 94539-5652, USA). The substrates were then cleaned in 3:1 $H_2SO_4:H_2O_2$ solution for at least 15 minutes prior to etching in forming gas. To etch the samples in forming gas, the substrates were placed onto an aluminum oxide plate and loaded into an Micropyretics Heaters International (MHI) tube furnace (Micropyretics Heaters International, Inc., 750 Redna Terrace, Cincinnati, OH 45215, USA) and heated with $MoSi_2$ heating elements. Insulating plugs were placed in each end of the tubes to improve thermal uniformity. Both the plugs and tube were made of aluminum oxide. The 4H—SiC substrates were etched at 1500° C., 1550° C., and 1600° C. in forming gas (4% $H_2$ in $N_2$ balance) with gas flows of either 5 or 20 standard cubic feet per hour (SCFH). In all etches, pure $N_2$ was flowed at 10 SCFH at temperatures below 1400° C. during both the heat up and cool down. The furnace was ramped to temperature at 5° C. per minute, held at temperature for one hour, and the power was then turned off to allow the furnace to cool naturally.

Scanning electron microscopy (Hitachi® S-800, Hitachi® America, Ltd., 2535 Augustine Dr., Santa Clara, CA 95054, USA; and Thermo Fisher Scientific® Apreo, Thermo Fisher Scientific®, 168 Third Avenue, Waltham, MA 02451, USA) was used to image the features before and after etching and to measure the lateral etch rates of the material. Energy dispersive spectroscopy was used for elemental analysis of the substrates.

Results

A. Etching of 4H—SiC Pillars

Figure 3:
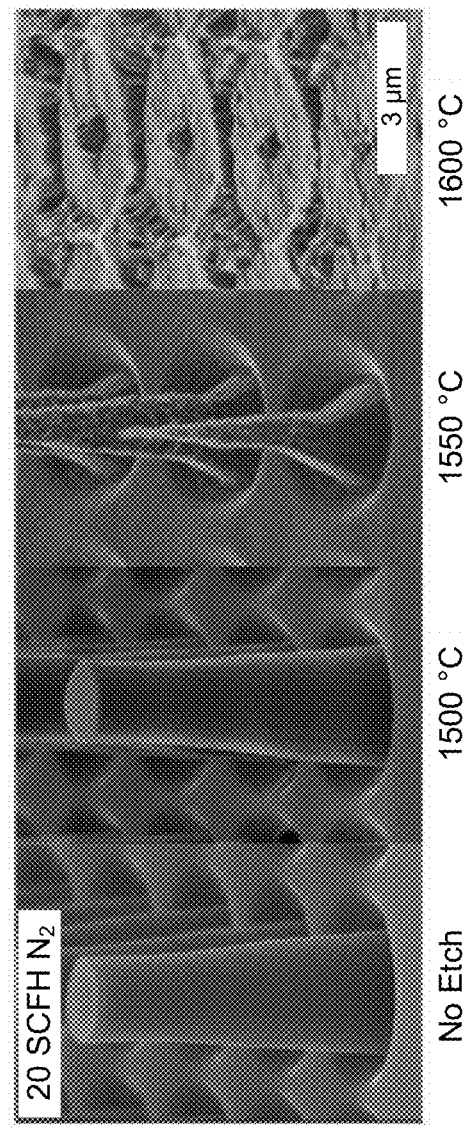
FIG. 3 is a perspective view of control samples before and after heating to 1500° C., 1550° C., and 1600° C. for 1 hour in 20 standard cubic feet per hour (SCFH) of pure $N_2$, according to one aspect of the presently disclosed inventive concepts.

FIG. 3 is a perspective view of control samples before and after heating to 1500° C., 1550° C., and 1600° C. for 1 hour in 20 SCFH of pure $N_2$. The etch rate at 1500° C. is minimal and the sharp edges at the top rim of the pillar and at the top of the trench on the floor have slightly rounded after annealing. The pillars begin to noticeably decompose at 1550° C. The pillar sidewall surfaces and the etched floor become rough. The pillars decompose increasingly faster as the temperature is increased. The decomposition of the pillars is nearly complete at 1600° C. with little of the pillars remaining.

Figure 4:
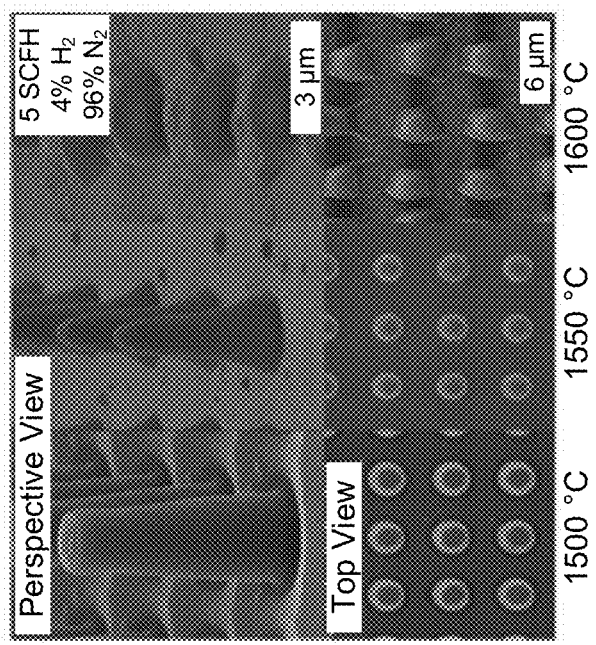
FIG. 4 is a perspective view and a top view of 4H—SiC pillars after etching in 5 SCFH of forming gas at 1500° C., 1550° C., and 1600° C. for 1 hour, according to one aspect of the presently disclosed inventive concepts.

When hydrogen is introduced through a 5 SCFH flow of flowing gas, the pillars begin to etch isotropically as shown in FIG. 4. FIG. 4 includes a perspective view and a top view of 2 μm wide and 5 μm tall 4H—SiC pillars after etching in 5 SCFH of forming gas at 1500° C., 1550° C., and 1600° C. for 1 hour. At 1500° C., the top of the pillar becomes domed and the trenches at the base of the pillar are strongly etched. On the floor, droplet-like features are randomly dispersed. When the etch temperature is increased at 1550° C., the pillars are shorter and have extremely rounded edges. The trenches surrounding the pillars have completely disappeared and the floor is covered with droplets varying in diameter from about 100 nm to several hundred nanometers. As the temperature is further increased to 1600° C., the pillars cease to exist, and large droplets (e.g., a few μm in diameter) appear on the surface.

Figure 5:
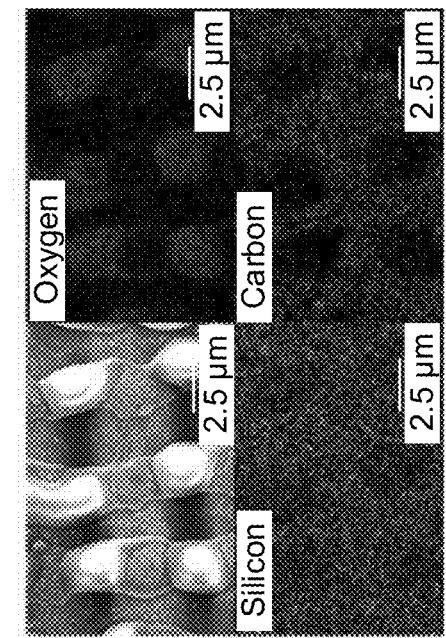
FIG. 5 is an energy dispersive spectroscopy (EDS) mapping of the 4H—SiC pillar surfaces after etching in 5 SCFH of forming gas at 1600° C. for 1 hour, according to one aspect of the presently disclosed inventive concepts.

To better identify the composition and origin of the droplets, top view energy dispersive spectroscopy (EDS) mapping was employed on the sample etched at 1600° C. The EDS mapping of the 4H—SiC pillar surface after etching in 5 SCFH of forming gas at 1600° C. for 1 hour is shown in FIG. 5. The map reveals that the droplets are oxygen-rich and contain silicon, indicating that the droplets are likely composed of silicon dioxide ($SiO_2$). The charging of the droplets in the scanning electron microscopy (SEM) image is consistent with poorly conductive $SiO_2$. The floor surrounding the droplets has a strong silicon and carbon signal representative of the SiC substrate. Carbon is not strongly detected in the droplets. Point scans on the droplets also reveal the presence of aluminum. The presence of aluminum indicates that the source of the oxygen is likely the aluminum oxide components of the furnace (e.g., the tube, the insulation, and/or the plate on which the sample is placed for etching). While oxygen was detected to a degree on the controls, the atomic percentage of oxygen present in the samples etched at 5 SCFH of forming gas is several times larger. The introduction of hydrogen into the furnace may be causing a chemical reduction of the aluminum oxide components and liberating oxygen. This oxygen may then oxidize the silicon carbon surface in a competing surface reaction with the hydrogen etching and form an involatile $SiO_2$ film. Since the etch temperatures are much higher than the melting point of $SiO_2$, the film is in a liquid state. This is consistent with the droplet morphology of the $SiO_2$ as shown in FIGS. 4 and 5 after cooling the samples. If the $SiO_2$ liquid film wets the SiC, then the etch is likely mediated by diffusion of the species through the film. A diffusion limited reaction may explain the isotropic etching of the SiC as the etch would no longer be controlled by surface kinetics at the SiC surface but by the isotropic diffusion through the $SiO_2$ film.

The introduction of oxygen caused the etching to be relatively more isotropic than in the absence of oxygen. The inventors were surprised to discover that oxygen during etching affected the isotropic nature of the etch. Moreover, the inventors were also surprised to learn that the isotropic nature of the etch with oxygen present is enhanced at lower flow rates of the gas. This phenomenon was unexpected. Without wishing to be bound by any particular theory, it is currently believed that a lower flow rate of the gas allows more time for the oxygen to react, whereas the oxygen is more likely to be swept away before reacting at higher flow rates.

Figure 7:
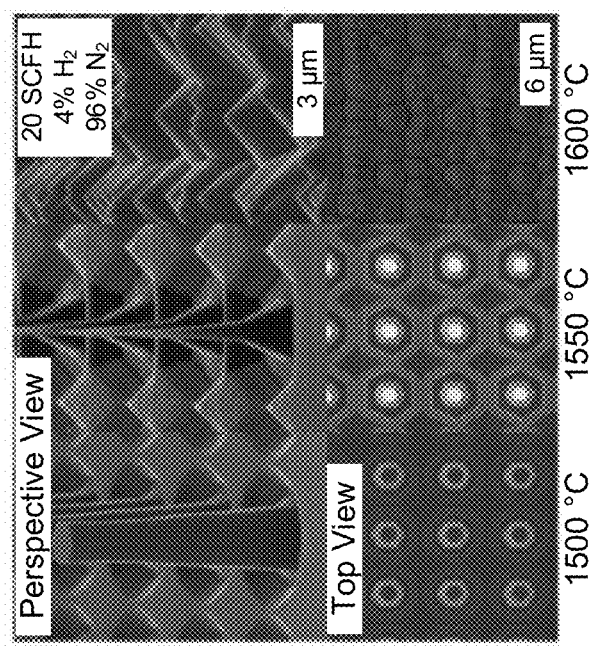
FIG. 7 is a perspective view of the of 4H—SiC tips fabricated by etching 2 µm wide pillars at 1550° C. for 1 hour, according to one aspect of the presently disclosed inventive concepts.
Figure 6:
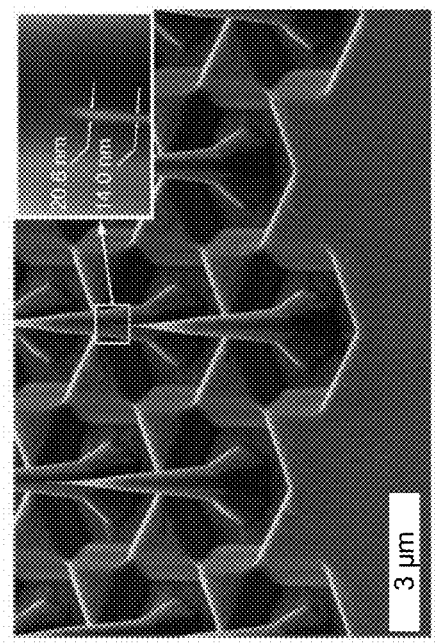
FIG. 6 is a perspective view and a top view of 4H—SiC pillars after etching in 20 SCFH of forming gas at 1500° C., 1550° C., and 1600° C. for 1 hour, according to one aspect of the presently disclosed inventive concepts.

To out-compete the oxidation of the SiC surface, the forming gas flow rate was increased to 20 SCFH. FIG. 6 includes perspective view and top view SEM images of pillars after etching. As the $H_2$ flux is increased, the etch changes from isotropic to anisotropic at 1500° C. and 1550° C. At 1500° C., the initially round pillars become hexagonal rods with faces parallel to the a-plane of the crystal. The round trenches at the base of the pillars become slightly hexagonal. When the temperature is increased to 1550° C., the lateral etch rate increases and the pillars become long tapered spikes. In the top view SEM micrograph in FIG. 6, the spikes are seen to be hexagonal with facets colinear with the a-planes. The trenches become increasingly hexagonal with faces colinear with the m-planes. The spikes were further imaged to reveal that the SiC tips narrow to as thin as 15 nm. The spikes are highlighted in FIG. 7. Specifically, FIG. 7 is a perspective view of the of 4H—SiC tips fabricated by etching 2 μm wide pillars at 1550° C. for 1 hour where the inset shows that the tips are as narrow as 15 nm in diameter. At 1600° C., the etch is no longer crystallographic and the pillars are etched into short, circular conical points (see FIG. 6). The pillars become conical points and the floor becomes covered with a similar morphology. At this temperature, the etch rates of different crystals planes may begin to converge, thus preventing m- or a-planes from forming.

B. Crystallographic Etch Rates of 4H— and 6H—SiC

Figure 8:
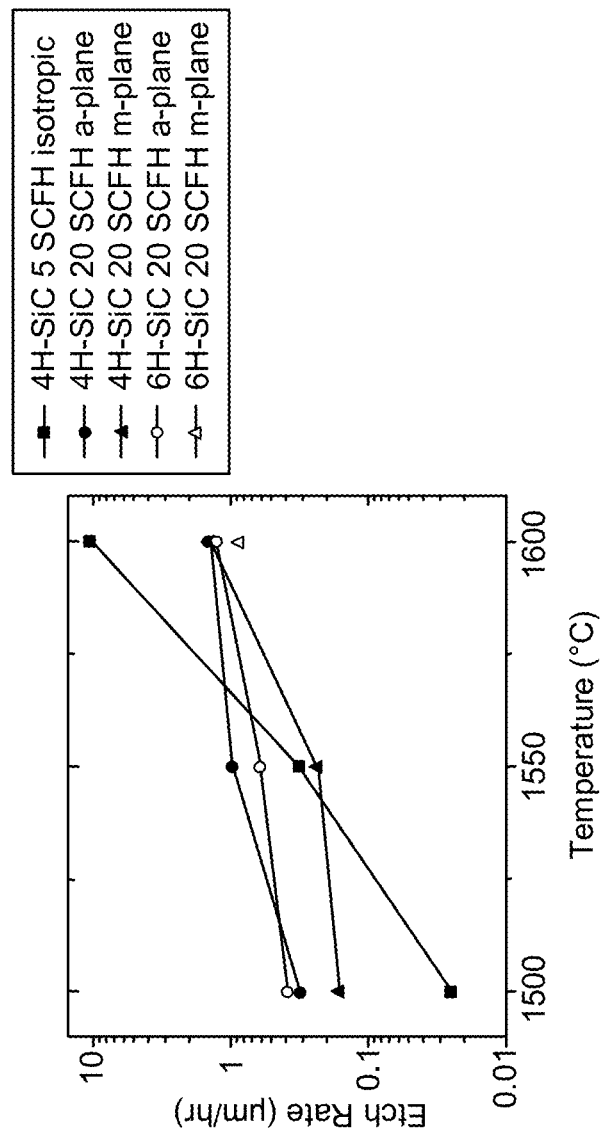
FIG. 8 is a graph of lateral etch rates measured as a function of temperature, polytype, and alignment along m-planes and a-planes of SiC structures, according to one aspect of the presently disclosed inventive concepts.

FIG. 8 is a graph of lateral etch rates measured as a function of temperature, polytype, and alignment along m-planes and a-planes of the SiC structures. To further investigate the crystallographic etching of the 3D, SiC structures, lateral etch rates were measured on 4H— and 6H—SiC substrates. Ridges oriented along different crystal planes were measured before and after etching to determine the etch rates. As noted above, no preferential etching of the m- or a-plane was observed, and the etch appears to be isotropic. The change in etch rate from 1500° C. and 1600° C. spans nearly three orders of magnitude from less than 100 nm/hour to over 10 μm/hr. The change in etch rates is much larger than the etches at 20 SCFH, consistent with the different etch mechanism described above for 5 SCFH as compared to 20 SCFH.

At 20 SCFH forming gas flow, the etch rates in the a-direction was similar for both 4H— and 6H—SiC and ranged from about 300-400 nm/hr to a little over 1 μm/hr. As the etch rate in the m-direction is very low at 1500° C. and 1550° C., only the 4H—SiC could be accurately measured in this direction. The m-direction etch rate is much lower than the a-direction with rates of about 160-230 nm/hr. At 1600° C., the etch rate in the m-plane markedly increased to around 1 μm/hr for both 4H— and 6H—SiC, similar to the etch rates in the a-direction in both materials. The convergence of the etch rates in the m- and a-directions is evident in the morphology of the 4H—SiC pillars after etching; the remaining cones on the surface are circular and do not exhibit a hexagonal habit.

Figure 9B:
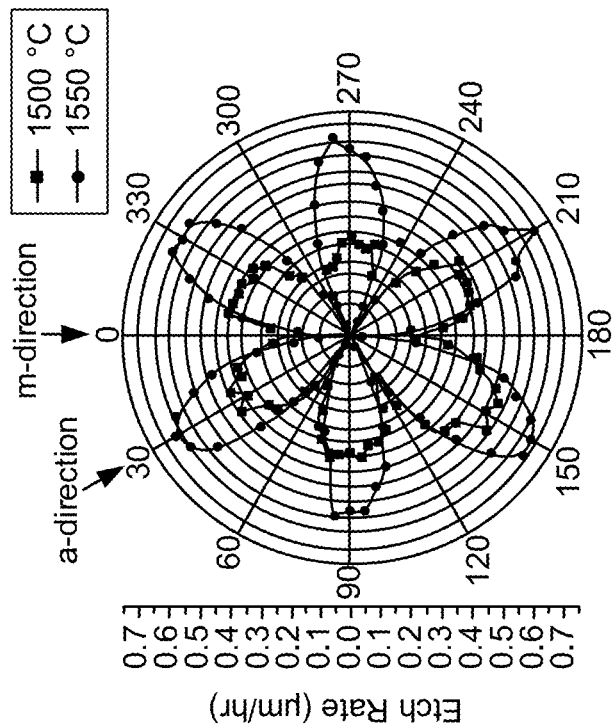
FIG. 9B is a graph of the measured lateral etch rate at 1500° C. and 1550° C. as a function of ridge orientation, according to one aspect of the presently disclosed inventive concepts.
Figure 9A:
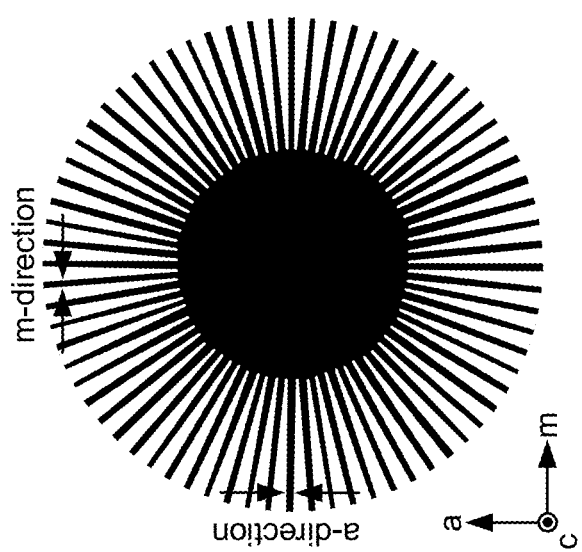
FIG. 9A is an optical image of a test pattern of ridges rotated every 5°, according to one aspect of the presently disclosed inventive concepts.

The lateral etch rate dependence on the orientation of the sidewall surface relative to the m- and a-planes was further explored by etching ridges rotated every 5° about the c-axis on 6H—SiC. An optical image of the test pattern of ridges rotated every 5° is shown in FIG. 9A. The measured lateral etch rate at 1500° C. and 1550° C. as a function of ridge orientation is shown in FIG. 9B. The widths of the ridges before and after etching were measured to determine lateral etch rates as a function of alignment to the m-planes and a-planes. The ridges were etched in 20 SCFH of forming gas at 1500° C. and 1550° C. The silicon carbide etches fastest where the ridges and sidewalls are aligned at one of the six a-planes. The hexagonal symmetry of the crystal is shown in FIG. 9B. As the sidewalls of the ridges become parallel to the a-plane, the lateral etch rate reaches a maximum. A minimum is reached when the sidewalls are aligned with m-planes.

The difference in the etch rate of the m- and a-planes may explain the transformation of circular pillars to hexagonal pillars after etching. The difference in etch rates may also explain why the etched trenches surrounding the pillars are hexagonal but rotated 30° relative to the pillar hexagon. As discussed above, the pillar facets are aligned along the a-planes. For convex surfaces, the faster etching plane will emerge and has been observed during etching in other hexagonal crystals such as GaN. Here, the a-plane etches faster and becomes the facet on the convexly shaped pillars. For concave surfaces, the slower etching facet emerges. In SiC, the m-plane etches more slowly, and the facets along the concave trench surrounding the pillars are accordingly aligned to the m-planes. This effect is further demonstrated in FIGS. 10A-10B.

Figure 10B:
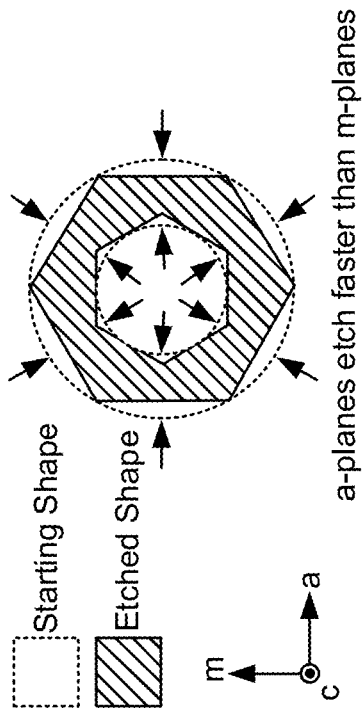
FIG. 10B is a schematic demonstrating the relationship between the etch rates and the morphology of the rings, according to one aspect of the presently disclosed inventive concepts.
Figure 10A:
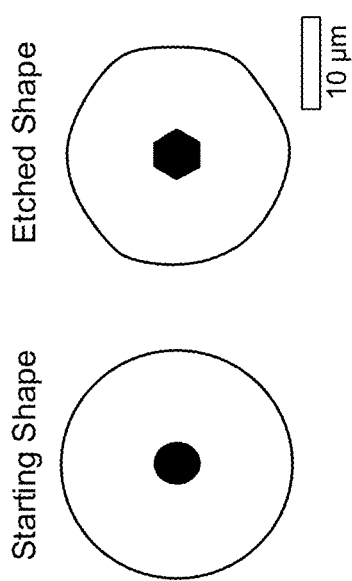
FIG. 10A are optical images of 6H—SiC rings before and after etching at 1550° C. for 1 hour in 20 SCFH, according to one aspect of the presently disclosed inventive concepts.

FIG. 10A are optical images of 6H—SiC rings before and after etching at 1550° C. for 1 hour in 20 SCFH. A ring-shaped mesa was fabricated onto a 6H—SiC substrate and subsequently etched at 1550° C. for 1 hour in 20 SCFH of forming gas. The ring is protruding out of the page. The inner concave hole in the ring becomes a hexagon with facets parallel to the m-plane after etching. The convex outer perimeter of the ring becomes a hexagon with facets parallel to the m-plane after etching. The convex outer perimeter of the ring becomes hexagonal with facets starting to form that are parallel to the a-plane.

Before etching, the inner and outer diameters of the ring are circular. After etching, the concave inner diameter becomes hexagonal with m-plane facets. The outer diameter also begins to adopt a hexagonal habit but where the facets are aligned to the a-planes.

FIG. 10B is a schematic which demonstrates when the a-plane etches faster than the m-plane. Concave surfaces become m-planes and convex surfaces become a-planes. A higher etch rate in the a-direction leads to the observed final morphology. The arrows show all the surfaces perpendicular to the a-plane on the ring mesa. The m-plane is known to be more stable than the a-plane and the m-plane has a higher density of dangling bonds than the m-plane in H-terminated 4H—SiC.

EXPERIMENTAL CONCLUSIONS

2 μm and 5 μm tall pillars were plasma-etched into 4H— and 6H—SiC substrates and subsequently etched in forming gas at 1500° C., 1550° C., and 1600° C. for 1 hour at 5 SCFH and 20 SCFH. At low forming gas flow rates, the pillars etched isotropically, assisted by oxidation from oxygen liberated from the aluminum oxide components of the tube furnace. The etch was likely mediated by a $SiO_2$ film that formed on the surface during the etch. At higher flow rates, the etch becomes crystallographic. The etch rates were measured and showed that the a-plane etches more quickly than the m-plane. This difference in etch rates leads to convex surfaces becoming faceted along the a-planes and concave surfaces become faceted along m-planes.

In Use

Etching pillars in forming gas is shown to be an effective method to fabricate extremely sharp points in SiC. Micro- and nano-needles have a variety of uses including field emission tips, atomic force microscopic probes, etc. SiC is attractive for field emission tips due its low electron affinity, high thermal conductivity, excellent chemical stability, etc. Field emission characteristics of these points may be measured for future applications. In general, the field enhancement is increased with sharper field emission tips (e.g., by concentrating the electric field to the point, the electrons are able to "hop off" onto the vacuum above, on, and/or outside the tip).

SiC is an attractive material for biological applications due to its chemical inertness and biocompatibility. For example, many materials corrode in living tissue. The "etch rate" of amorphous silicon carbide as presented herein is extremely low compared to other materials such as silicon nitride. Crystalline SiC is more stable and less likely to corrode in tissue. SiC nanoneedles, including SiC nanosyringes, may be used in biomedical applications such as for transdermal delivery of drugs and/or proteins. For example, SiC nanoneedles may be beneficial to reduce the toxicity and/or damage caused by traditional transdermal delivery of drugs and/or proteins to delicate body tissues (e.g., muscle tissue, nervous tissue, etc.). In contrast, conventional carbon nanotubes are cytotoxic. In other applications, SiC nanoneedles may be used to deliver transdermal sensors for biosensing and stimulation such as deep neural probes. SiC nanoneedles, including SiC nano-syringes, may be used to extract samples from body tissues and/or cells. In some applications, SiC nanoneedles may be used for electronic probing inside a cell for taking biological measurements and/or investigating the inner processes of the cell. In various approaches, SiC nanoneedles formed according to the various aspects described herein comprise rounded tips. Rounded tips would be beneficial to prevent puncture of cell walls in delicate procedures. SiC nanoneedles may be used to develop and/or perform minimally invasive biomedical procedures, treatments, experiments, etc. Hollow SiC tips may be used as patch clamps for measurements on fluids, ions, and voltages at cell surfaces. The ability to tune the sharpness of the tip allows for the patch clamp to function in different modes. An isotropically-etched tip will be rounded and can seal to the surface of a cell membrane for measurements of single ion channels, etc. The anisotropically-etched tips will be sharp and can be used to penetrate the cell membrane to interface with the interior of the cell.

In various aspects, it would be desirable to use the crystallographic nature of the sharp SiC tips for controlling interactions at the interfaces of the tips. For example, the atomically smooth surfaces of the crystallographic tips may be particularly useful for epitaxy on 3D structures or structures which do not have purely horizontal surfaces. Formation techniques for various epitaxial structures may benefit from the crystallographic etching of SiC as described herein.

Various operations of the present disclosure may be useful for electronic applications using SiC. The process described herein may be adapted for semiconductors such as diamond as would be understood by one having ordinary skill in the art in view of the present disclosure.

The inventive concepts disclosed herein have been presented by way of example to illustrate the myriad features thereof in a plurality of illustrative scenarios, aspects, and/or implementations. It should be appreciated that the concepts generally disclosed are to be considered as modular, and may be implemented in any combination, permutation, or synthesis thereof. In addition, any modification, alteration, or equivalent of the presently disclosed features, functions, and concepts that would be appreciated by a person having ordinary skill in the art upon reading the instant descriptions should also be considered within the scope of this disclosure.

While various aspects have been described above, it should be understood that they have been presented by way of example only, and not limitation. Thus, the breadth and scope of an aspect of the present invention should not be limited by any of the above-described exemplary aspects, but should be defined only in accordance with the following claims and their equivalents.

What is claimed is:

1. A product, comprising:
   an elongated carbon-containing pillar having a bottom and a tip opposite the bottom,
   wherein the width of the pillar measured 1 nm below the tip is less than 700 nm,
   wherein the pillar, when formed, has no oxidation on an outer surface thereof.

2. The product as recited in claim 1, wherein the tip is rounded.

3. The product as recited in claim 1, wherein the pillar extends from a single crystal substrate having a bulk composition that is the same as the bulk composition of the pillar.

4. The product as recited in claim 3, wherein the pillar has no higher concentration of defects per unit volume than the single crystal substrate.

5. The product as recited in claim 1, wherein the pillar has a faceted peripheral outer surface.

6. The product as recited in claim 1, wherein the pillar has a rounded peripheral outer surface.

7. The product as recited in claim 6, wherein the peripheral outer surface of the pillar is rounded therealong from the bottom to the tip of the pillar.

8. The product as recited in claim 1, wherein the pillar is SiC.

9. The product as recited in claim 1, wherein the pillar is diamond.

10. The product as recited in claim 1, comprising an array of the pillars extending from a substrate, the pillars and substrate having the same bulk composition throughout.

11. The product as recited in claim 10, wherein at least some of the pillars have an inner channel extending along a longitudinal axis thereof.

12. The product as recited in claim 11, wherein the substrate has channels therethrough in fluid communication with the channels of at least some of the pillars.

13. A method of making the product as recited in claim 1, the method comprising:
    masking a carbon-containing single crystal for defining masked regions and unmasked regions on the single crystal;
    performing a plasma etch for removing portions of the unmasked regions of the single crystal, thereby defining a pillar in each unmasked region; and
    performing a chemical etch on the pillars at a temperature between 1200° C. and 1600° C. for selectively reducing a width of each pillar.

14. The method as recited in claim 13, wherein performing the chemical etch includes contacting the pillars with a gas having at least one etchant, the etchant being selected from the group consisting of: H, Cl, Br, and I.

15. The method as recited in claim 14, comprising adding a defined amount of oxygen to the gas for reducing an extent of crystallographic etching.

16. The method as recited in claim 13, wherein each pillar comprises a bottom and a tip opposite the bottom, wherein the width of the pillar measured 1 nm below the tip is less than 700 nm.

17. The method as recited in claim 13, wherein each pillar has an inner channel extending along a longitudinal axis thereof.

18. A product, comprising:
    an elongated carbon-containing pillar having a bottom and a tip opposite the bottom,
    wherein the width of the pillar measured 1 nm below the tip is less than 700 nm,
    wherein the pillar has an inner channel extending along a longitudinal axis thereof.

19. The product as recited in claim 18, wherein the pillar extends from a single crystal substrate having a bulk composition that is the same as the bulk composition of the pillar, wherein the substrate has a channel therethrough in fluid communication with the channel of the pillar.

* * * * *